United States Patent
Henry et al.

(10) Patent No.: US 8,206,450 B2
(45) Date of Patent: Jun. 26, 2012

(54) COMPOSITE IMPLANTS AND METHODS OF MAKING AND USING THE SAME

(75) Inventors: Sebastien Henry, Smyrna, GA (US); William Graham Midgette, Grayson, GA (US); Sejdefa Dozic, Atlanta, GA (US); Kent Iversen, LaGrange, GA (US); Guoqiang Mao, Smyrna, GA (US); John Randolph Miller, Glen Ellyn, IL (US)

(73) Assignee: Howmedica Osteonics Corp., Mahwah, NJ (US)

( * ) Notice: Subject to any disclaimer, the term of this patent is extended or adjusted under 35 U.S.C. 154(b) by 245 days.

(21) Appl. No.: 12/356,230

(22) Filed: Jan. 20, 2009

(65) Prior Publication Data

US 2010/0023130 A1    Jan. 28, 2010

Related U.S. Application Data

(60) Provisional application No. 61/022,113, filed on Jan. 18, 2008.

(51) Int. Cl.
*A61F 2/02* (2006.01)

(52) U.S. Cl. ............... 623/17.18; 623/17.17; 623/17.19; 623/23.58

(58) Field of Classification Search .... 623/17.17–17.19, 623/14.12, 13.11
See application file for complete search history.

(56) References Cited

U.S. PATENT DOCUMENTS

| | | | |
|---|---|---|---|
| 4,955,909 A | 9/1990 | Ersek et al. | |
| 5,067,965 A | 11/1991 | Ersek et al. | |
| 5,422,150 A * | 6/1995 | Scoular et al. | 428/33 |
| 5,496,371 A | 3/1996 | Eppley et al. | |
| 5,545,226 A | 8/1996 | Wingo et al. | |
| 6,268,405 B1 * | 7/2001 | Yao et al. | 523/113 |
| 6,277,150 B1 * | 8/2001 | Crawley et al. | 623/17.18 |
| 2006/0224242 A1 | 10/2006 | Swords et al. | |
| 2007/0293947 A1 | 12/2007 | Mansmann | |
| 2008/0017569 A1 * | 1/2008 | Ramsey et al. | 210/490 |

FOREIGN PATENT DOCUMENTS

EP    1216717 A1    6/2002
WO    2006112678 A1    10/2006

* cited by examiner

*Primary Examiner* — Thomas J Sweet
*Assistant Examiner* — Brian Dukert
(74) *Attorney, Agent, or Firm* — Lerner, David, Littenberg, Krumholz & Mentlik, LLP

(57) ABSTRACT

The present invention provides composite implants for the replacement or augmentation of non-load bearing or load bearing soft tissues, and methods of making and using these implant compositions. In one embodiment, a composite implant of the present invention comprises a soft polymeric component coupled to a porous polymeric substrate.

27 Claims, 13 Drawing Sheets

COMPOSITE IMPLANTS AND METHODS OF MAKING AND USING THE SAME

PRIOR RELATED APPLICATIONS

This patent application claims the benefit of priority of U.S. provisional patent application Ser. No. 61/022,113 filed Jan. 18, 2008, which is incorporated herein by reference in its entirety.

FIELD OF THE INVENTION

The present invention relates to implant compositions for the replacement or augmentation of load bearing and non-load bearing soft tissues, and methods of making and using these implant compositions.

BACKGROUND OF THE INVENTION

Various implant compositions have been used subcutaneously to augment or replace soft tissues thereby rendering cosmetic enhancements to an individual. Many of these implant compositions demonstrate non-porous surfaces, which do not allow for cellular and tissue growth into the implant composition. The inability to support cellular and tissue ingrowth has several disadvantages. One disadvantage, in particular, is associated with implant stability. Non-porous implant compositions unable to support cellular and tissue ingrowth can migrate from the implant site leading to unsatisfactory cosmetic or aesthetic results and undesirable tissue resorption. Motion or migration of an implant, for example, may result in bone resorption at the implant/bone interface.

Moreover, several prior implant compositions for augmentation or replacement of non-load bearing tissues are rigid and bulky. As a result, procedures for their implantation in a patient require large incisions leading to undesirable cosmetic results and longer periods of healing. Attempts have been made to minimize sites of incision by dividing implants into smaller pieces prior to implantation. While the division of an implant into smaller pieces can decrease the size of a required incision, such a procedure produces additional problems. Dividing an implant into a plurality of pieces for insertion, for example, can increase the likelihood of implant migration and result in surface inconsistencies due to gaps between the individual implant pieces.

In view of the foregoing disadvantages, it would be desirable to provide implant compositions operable to reduce tissue resorption and maintain minimal incision sizes without the requirement of implant sectioning. It would additionally be desirable to provide methods of producing and using such implant compositions.

SUMMARY

The present invention provides composite implants which overcome the foregoing disadvantages. The present invention provides composite implants and methods of making and using the same for the replacement and/or augmentation of non-load bearing and load bearing soft tissues. The composite implants comprise a soft polymeric component coupled to a porous polymeric substrate. Composite implants of the present invention, in some embodiments, can reduce or preclude implant motion by permitting cell migration and tissue growth into the implant. The reduction of implant motion reduces or eliminates tissue resorption at an implant/tissue interface such as a bone/implant interface. Moreover, composite implants of the present invention, in some embodiments, are flexible and/or foldable allowing the implant to assume a smaller size for implantation procedures. Once in the implantation site, the folded implant can unfold and resume the size or configuration prior to folding. The foldable nature of the composite implant can permit smaller incision sizes during implantation procedures while precluding the need for implant sectioning.

In one embodiment, the present invention provides a composite implant comprising a soft polymeric component coupled to a porous polymeric substrate. In some embodiments, these composite implants are load bearing implants. In some embodiments, these composite implants are non-load bearing implants. In one embodiment the non-loading bearing composite implants are craniofacial implants. In some embodiments, the craniofacial implants are eye, chin, ear, malar or nose implants. Other composite implants of the present invention include but are not limited to muscle implants, breast implants, gluteal implants, palatine implants, and osseomuscle implants. The implants of the present invention may be used to augment muscle and other tissues that may be damaged due to trauma or disease, or removed by surgery. For example, removal of an osseomuscle flap from the fibula for use in mandibular repair leaves a deficit at the site of flap removal which may be supplemented with these composite implants. The term "soft," as used herein, refers to the mechanical properties of soft tissues of a mammal. In some embodiments, soft, non-load bearing tissues of a mammal comprise, for example, muscle tissue, adipose tissue, fascia, or blood vessels. Soft tissues also include without limitation fibrous tissues such as cartilage, tendons and ligaments, some of which are load bearing. The composite implants of this invention may also be used in nasopharyngeal or laryngeal applications, for example, for replacement or augmentation of the cartilage found in the nasopharynx and the larynx.

The soft polymeric component of a composite implant, according to embodiments of the present invention, demonstrates mechanical properties consistent with soft, non-load bearing tissues of a mammalian body. In some embodiments, for example, the soft polymeric component of an implant has a Shore A hardness greater than about 20, or greater than about 30. In some embodiments, the soft polymeric component of an implant has a Shore A hardness less than about 80.

A soft polymeric component in some embodiments of a composite implant comprises at least one polymeric layer. In other embodiments, a soft polymeric component comprises a plurality of polymeric layers. Moreover, in one embodiment, a soft polymeric component of a composite implant is non-porous or substantially non-porous. In another embodiment, a soft polymeric component is porous.

In some embodiments, a porous polymeric substrate comprises at least one porous polymeric layer. In another embodiment, a porous polymeric substrate comprises a plurality of porous polymeric layers. In some embodiments, a porous polymeric substrate comprises a plurality of sintered polymeric particles.

A porous polymeric substrate, according to some embodiments of the present invention, facilitates cell migration and tissue growth into and/or within the composite implant. The porous polymeric substrate, in some embodiments, demonstrates a porosity and pore structure operable to facilitate soft tissue ingrowth and/or hard tissue ingrowth. In one embodiment, for example, a porous polymeric substrate of a composite implant is placed in contact with bone at an implant site and facilitates osteoprogenitor cell migration, such as osteoblast migration, into the composite implant for subsequent growth of bone. Cellular and tissue ingrowth, as provided herein, can stabilize the composite implant thereby reducing tissue resorption at implant/host tissue interfaces.

The porous polymeric substrate, in some embodiments, is rigid. In other embodiments, the porous polymeric substrate is flexible. Moreover, the porous polymeric substrate, in some embodiments, is coextensive or substantially coextensive with the soft polymeric component. In other embodiments, the porous polymeric substrate is not coextensive with the soft polymeric component.

Composite implants of the present invention are well suited for a variety of applications, including without limitation the replacement and/or augmentation of craniofacial tissues. In one embodiment, the soft polymeric component can replace or augment soft facial tissue while the porous polymeric substrate can contact the underlying craniofacial bone and support growth of bone into the implant for implant stabilization.

In another aspect, the present invention provides methods of producing a composite implant comprising a soft polymeric component and a porous polymeric substrate. In one embodiment, a method of producing a composite implant comprises providing a soft polymeric component, providing a porous polymeric substrate, and coupling the soft polymeric component to the porous polymeric substrate. In some embodiments, providing a porous polymeric substrate comprises providing a plurality of polymeric particles and sintering the plurality of polymeric particles. Moreover, coupling the soft polymeric component to the porous polymeric substrate, in some embodiments, comprises at least partially penetrating a plurality of pores of the porous polymeric substrate with the soft polymeric component. In other embodiments, coupling the soft polymeric component to the porous polymeric substrate comprises providing an adhesive component and interposing the adhesive component between the soft polymeric component and the porous polymeric substrate.

In another embodiment, a method of producing a composite implant comprises filling the mold with a liquid form soft polymeric component, adding a preformed porous polymeric component and having part of the porous polymeric component contacted to or inserted into the soft polymeric component, and curing and solidifying the soft polymeric component to the porous polymeric component. In one embodiment, curing and solidifying is a freeze and thaw process. In another embodiment, curing and solidifying is a heating process. In some embodiments, providing a porous polymeric component comprises providing a plurality of polymeric particles and sintering the plurality of polymeric particles. Moreover, coupling the soft polymeric component to the porous polymeric component, in some embodiments, comprises at least partially penetrating a plurality of pores of the porous polymeric substrate with the soft polymeric component.

In another embodiment, a method of producing a composite implant comprises filling the bottom part of a cavity of a mold with a liquid form soft polymeric component, adding polymeric particles on the top of the liquid form soft polymeric component in the cavity and filling the mold cavity, closing the mold cavity, heating the mold in an oven or a hot press, curing and solidifying the soft polymeric component, sintering polymeric particles into a porous substrate and coupling the soft polymeric component to the porous polymeric substrate simultaneously in the mold cavity. In some embodiments, the soft polymeric component at least partially penetrates a plurality of pores of the porous polymeric substrate.

In a further aspect, the present invention provides methods of treating a patient in need of an implant. In one embodiment, a method of treating a patient in need of an implant comprises providing a composite implant of the present invention comprising a soft polymeric component coupled to a porous polymeric substrate, providing access to an implant site and inserting the implant into an implant site of the patient. In some embodiments the implant may be folded before it is inserted into the implant site.

These and other objects, features and advantages of the present invention will become apparent after a review of the following detailed description of the disclosed embodiments and claims

DETAILED DESCRIPTION

Figure 1:
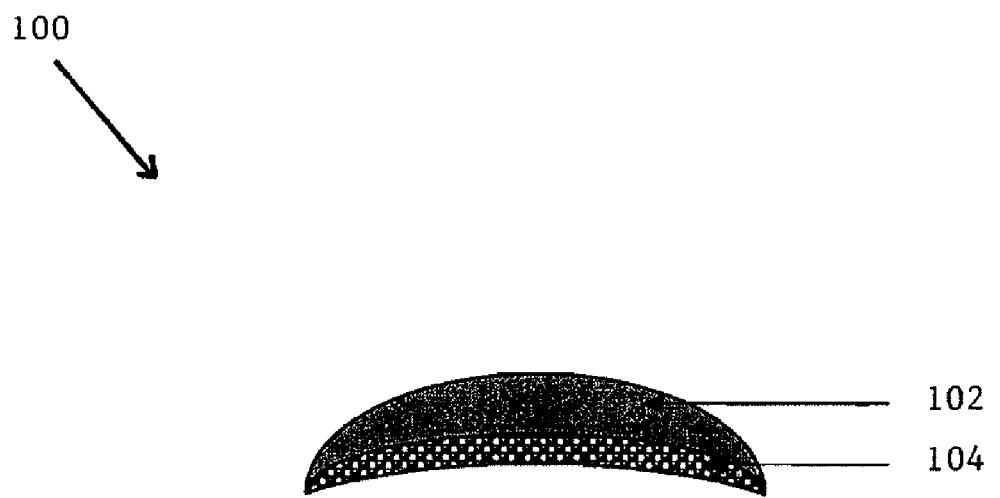
FIG. 1 illustrates an implant according to one embodiment of the present invention.

The present invention provides composite implants and methods of making and using the same for the replacement and/or augmentation of non-load bearing and load bearing soft tissues. The composite implants comprise a soft polymeric component coupled to a porous polymeric substrate.

Composite implants of the present invention, in some embodiments, can reduce or preclude implant motion by permitting cell migration and tissue growth into the implant. The reduction of implant motion reduces or eliminates tissue resorption at an implant/tissue interface such as a bone/implant interface. Moreover, composite implants of the present invention, in some embodiments, are flexible and/or foldable allowing the implant to assume a smaller size for implantation procedures. Once in the implantation site, the folded implant can unfold and resume the size or configuration prior to folding. The foldable nature of the composite implant can permit smaller incision sizes during implantation procedures while precluding the need for implant sectioning.

In a further aspect, the present invention provides methods of treating a patient in need of an implant. In one embodiment, a method of treating a patient in need of an implant comprises providing a composite implant of the present invention comprising a soft polymeric component coupled to a porous polymeric substrate, providing access to an implant site and inserting the implant into an implant site of the patient. In some embodiments the implant may be folded before it is inserted into the implant site.

Composite Implants

In one embodiment, the present invention provides a composite implant comprising a soft polymeric component coupled to a porous polymeric substrate. In some embodiments, these composite implants are load bearing implants. In some embodiments, these composite implants are non-load bearing implants. In one embodiment the non-loading bearing composite implants are craniofacial implants. In some embodiments, the craniofacial implants are eye, chin, ear, malar or nose implants. Other composite implants of the present invention include but are not limited to muscle implants, breast implants, gluteal implants, palatine implants, or osseomuscle implants. The implants of the present invention may be used to augment muscle and other tissues that may be damaged due to trauma or disease, or removed by surgery. For example, removal of an osseomuscle flap from the fibula for use in mandibular repair leaves a deficit at the site of flap removal which may be supplemented with these composite implants. The term "soft," as used herein, refers to the mechanical properties of soft tissues of a mammal. In some embodiments, soft, non-load bearing tissues of a mammal comprise muscle tissue, adipose tissue, fascia, or blood vessels. Soft tissues also include fibrous tissues such as cartilage, tendons and ligaments, some of which are load bearing. The composite implants of this invention may also be used in nasopharyngeal or laryngeal applications, for example, for replacement or augmentation of the cartilage found in the nasopharynx and the larynx.

FIG. 1 illustrates an implant according to one embodiment of the present invention. The composite implant (100) of FIG. 1 comprises a non-porous soft polymeric component (102) coupled to a porous polymeric substrate (104), wherein the porous polymeric substrate (104) is coextensive with the soft polymeric component (102). The thicknesses of the soft polymeric component (102) and the porous polymeric substrate (104) vary over the width of the composite implant (100). Moreover, the porous construction of the porous polymeric substrate (104) facilitates cell migration and tissue growth into the substrate (104). The porous polymeric substrate (104), in some embodiments, for example, can be placed adjacent to bone in a craniofacial implant site thereby facilitating growth of bone into the substrate (104). The non-porous construction of the soft polymeric component (102), however, does not support cell migration or tissue growth into the soft polymeric component.

Figure 2:
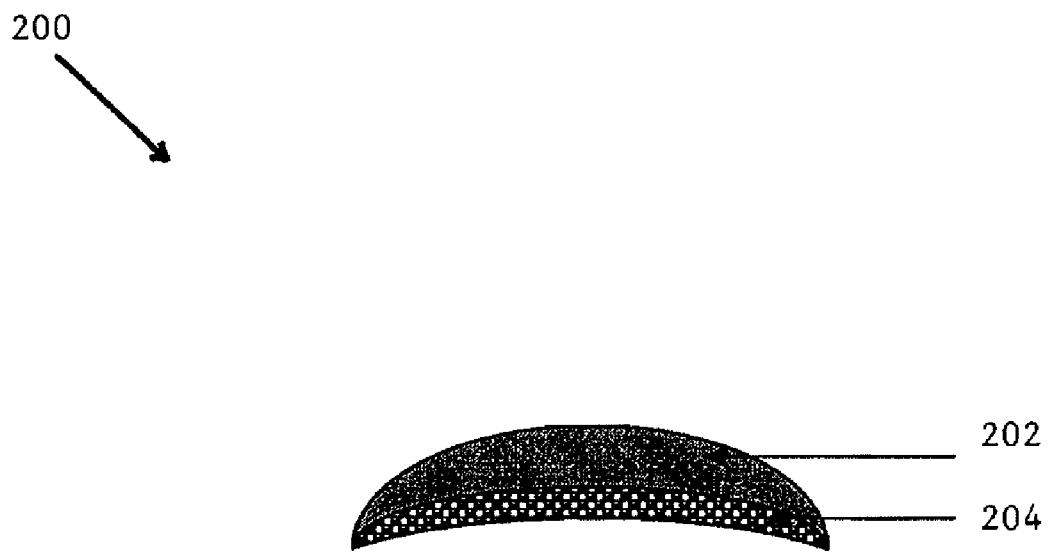
FIG. 2 illustrates an implant according to one embodiment of the present invention.

FIG. 2 illustrates an implant according to another embodiment of the present invention. The composite implant (200) of FIG. 2 comprises a soft polymeric substrate (202) coupled to a porous polymeric substrate (204), wherein the porous polymeric substrate (204) is coextensive with the soft polymeric component (202). The thicknesses of the soft polymeric component (202) and the porous polymeric substrate (204) vary over the width of the composite implant (200). The soft polymeric component (202) in the embodiment illustrated in FIG. 2 is porous thereby allowing cell migration and tissue growth into the soft polymeric component. The porous polymeric substrate (204) additionally permits cell migration and tissue growth into the substrate.

Figure 3:
FIG. 3 illustrates an implant according to one embodiment of the present invention.

FIG. 3 illustrates a composite implant according to one embodiment of the present invention wherein the porous polymeric substrate is not coextensive with the soft polymeric component. As illustrated in FIG. 3, the porous polymeric substrate (304) of the composite implant (300) does not cover the entire surface of the soft polymeric component (302).

As provided herein, in some embodiments, composite implants of the present invention are flexible and/or foldable. The foldable nature of a composite implant, according to some embodiments, permits the implant to assume a smaller size or reduced volume for implantation procedures. Once in the implantation site, the folded implant can unfold or be unfolded and resume the size or volume of the implant prior to folding. The foldable nature of a composite implant can permit smaller incision sizes and/or openings for implantation. As a result, composite implants of the present invention can be well suited for craniofacial applications where smaller incisions are desirable. In various embodiments, for example, a composite implant of the present invention is a malar implant, a chin implant, an eye implant, an ear implant or a nose implant.

Figure 4:
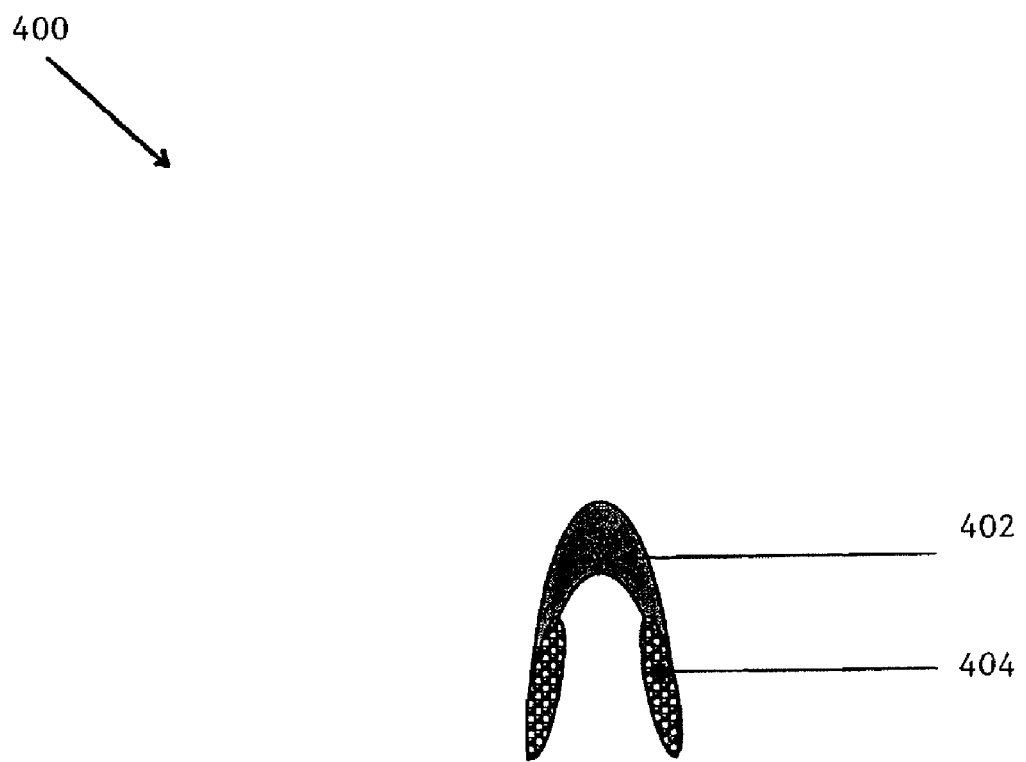
FIG. 4 illustrates an implant in a folded configuration according to one embodiment of the present invention.

In one embodiment, a composite implant can be folded approximately in half. In some embodiments, the flexible properties of a composite implant permit the implant to be folded in any desired configuration. FIG. 4 illustrates a composite implant in a folded configuration according to one embodiment of the present invention. The folded composite implant (400) in FIG. 4 comprises a porous polymeric substrate (404) that is not coextensive with the soft polymeric component (402). In such an embodiment, the porous polymeric substrate (404) demonstrates rigid mechanical properties without limiting or inhibiting the foldable nature of the composite implant (400).

Soft Polymeric Component

Turning now to components that can be included in composite implants of the present invention, composite implants of the present invention comprise a soft polymeric component. In some embodiments, the soft polymeric component comprises at least one polymeric layer. In other embodiments, the soft polymeric component comprises a plurality of polymeric layers.

Polymers suitable for use in one or more polymeric layers of a soft polymeric component, in some embodiments, comprise a polysiloxane, poly(vinyl alcohol), poly(vinyl alcohol) hydrogel, polytetrafluoroethylene (PTFE), expanded-polytetrafluoroethylene (e-PTFE), or polyurethane, or combinations thereof.

In some embodiments, a poly(vinyl alcohol) or poly(vinyl alcohol) hydrogel for use in the soft polymeric component has a molecular weight ranging from about 100,000 to about 500,000. In another embodiment, a poly(vinyl alcohol) or poly(vinyl alcohol) hydrogel has a molecular weight ranging from about 120,000 to about 200,000 or from about 140,000 to about 190,000. In some embodiments, a poly(vinyl alcohol) or poly(vinyl alcohol) hydrogel has a molecular weight ranging from about 10,000 to about 100,000. Moreover, a poly(vinyl alcohol) or poly(vinyl alcohol) hydrogel can have a degree of polymerization of at least 1,000 or at least 1,500. In one embodiment, a poly(vinyl alcohol) or poly(vinyl alcohol) hydrogel has a degree of polymerization of at least 1700.

A poly(vinyl alcohol) or poly(vinyl alcohol) hydrogel suitable for use in some embodiments of the present invention has a degree of hydrolysis of at least 95%. In other embodiments, a poly(vinyl alcohol) or poly(vinyl alcohol) hydrogel has a degree of hydrolysis of at least 98% or at least 99%.

In some embodiments, a polysiloxane suitable for use in the soft polymeric component of a composite implant has a degree of polymerization of at least 1,000. In other embodiments, a polysiloxane has a degree of polymerization of at least 1,500 or at least 2,000.

As provided herein, in some embodiments, the soft polymeric component of a composite implant of the present invention can have mechanical properties similar to or consistent with soft mammalian tissues. In some embodiments, the soft polymeric component has a Shore A hardness greater than about 20, or greater than about 30. In some embodiments, the soft polymeric component has a Shore A hardness of less than about 80. In other embodiments, the soft polymeric component has a Shore A hardness ranging from about 30 to about 70. In another embodiment, the soft polymeric component has a Shore A hardness ranging from about 40 to about 60. Hardness of the soft polymeric component can be determined according to ASTM D2240. Additionally, in some embodiments, the soft polymeric component has a tensile strength ranging from about 3 MPa to about 10 MPa. In some embodiments, the soft polymeric component is flexible and/or foldable.

The soft polymeric component, according to some embodiments, comprises a compositional gradient. In one embodiment, for example, the soft polymeric component comprises a first layer of a first polymer and a second layer of a second polymer, wherein the first and second polymers are different. Embodiments of soft polymeric components of the present invention contemplate any number of layers of different polymers arranged in any order.

Compositional gradients can allow tailoring of the soft polymeric component to the individual characteristics of the implant site. A first polymeric material such as a poly(vinyl alcohol) hydrogel, in one embodiment, for example, may provide bulk mechanical properties similar to or consistent with the soft tissues of the implant site while a second polymeric material such as e-PTFE may provide advantageous interfacial interactions with the tissues surrounding the implant. As a result, the soft polymeric layer can be constructed with a poly(vinyl alcohol) hydrogel layer covered by an e-PTFE layer for interaction with tissues surrounding the implant.

Additionally, in another embodiment, a first polymeric material may be operable to form advantageous interactions with the porous polymeric substrate or intervening adhesive layer, and a second polymeric material may provide mechanical properties similar to or consistent with the soft tissue of the implant site. As a result, the soft polymeric component can be constructed of an interior layer of the first polymeric material for coupling the soft polymeric component to the porous polymeric substrate and an exterior layer of the second polymeric material for augmenting or replacing tissues at the implant site.

In some embodiments, the soft polymeric component is non-porous or substantially non-porous. In such non-porous embodiments, the soft polymeric component does not support cell migration or tissue ingrowth. In other embodiments, the soft polymeric component is porous. In one embodiment, a porous soft polymeric component has an average pore size ranging from about 1 µm to about 1 mm. In another embodiment, a porous soft polymeric component has an average pore size ranging from about 10 µm to about 500 µm or from about 100 µm to about 300 µm. In some embodiments, a porous soft polymeric component has an average pore size ranging from about 25 µm to about 100 µm.

In some embodiments wherein the soft polymeric component is porous, the soft polymeric component has a porosity ranging from about 10% to about 90%. In other embodiments, a soft polymeric component has a porosity ranging from about 20% to about 80% or from about 30% to about 70%. In some embodiments, a soft polymeric component has a porosity less than about 10% or greater than about 90%.

A soft polymeric component, according to some embodiments, has a porosity gradient. In one embodiment, for example, the soft polymeric component of a composite implant comprises a region proximate the porous polymeric substrate and a region distal to the porous polymeric substrate wherein the region proximate the porous polymeric substrate has a porosity less than the region distal to the porous polymeric substrate. Such an arrangement can allow the soft polymeric component to provide a porosity and pore structure suitable for allowing cell migration and tissue growth into the soft polymeric component while retaining a less porous surface operable to increase the contact area with the porous polymeric substrate.

Alternatively, in another embodiment, the region of the soft polymeric component proximate the porous polymeric substrate has a porosity greater than the region of the soft polymeric component distal to the porous polymeric substrate. Such an arrangement, in some embodiments, permits the soft polymeric component to be resistant to cell migration and tissue ingrowth while providing a porous surface for infiltration by an adhesive component coupling the soft polymeric component to the porous polymeric substrate.

Figure 5:
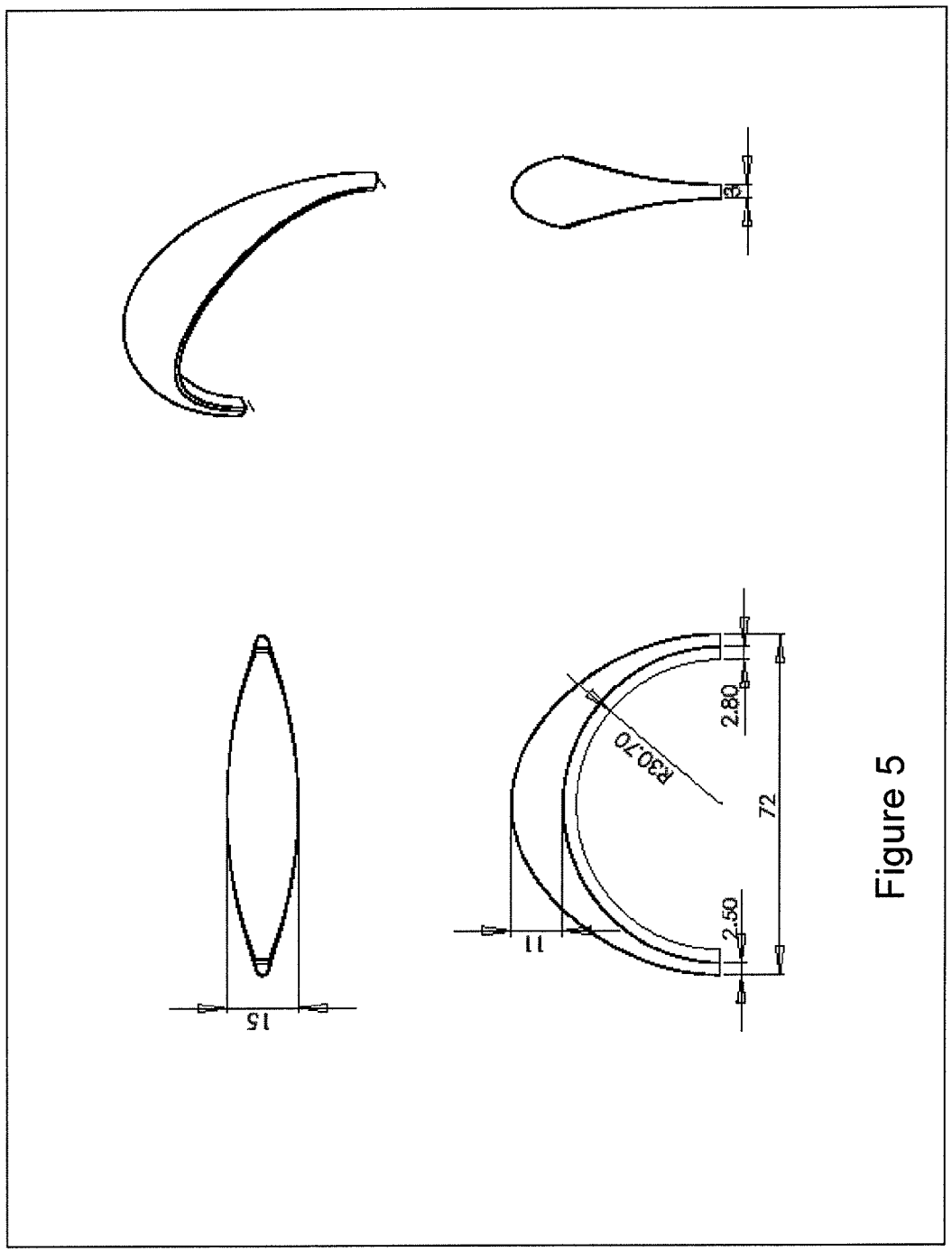
FIG. 5 illustrates an example of a chin implant according to the present invention.

Additionally, the soft polymeric component of a composite implant can have any desired length, width, and thickness. The length, width, and thickness of the soft polymeric component can depend on the shapes and dimensions of the implant site and/or the application of the implant such as craniofacial applications. In one embodiment, a chin implant is illustrated in FIG. 5, wherein the soft polymeric component can have a thickness of ranging from about 0.5 mm to about 15 mm. In other embodiments, the soft polymeric component can have a thickness of ranging from about 0.2 mm to about 10 mm or about 0.2 mm to about 100 mm. In other embodiments, the soft polymeric component can have a thickness greater than about 15 mm or less than about 0.5 mm. Moreover, the thickness of the soft polymeric component can vary over the length and/or width of the soft polymeric component. A soft polymeric component, in one embodiment, for example, can have a thickness of about 0.5 mm at an edge and a thickness of about 15 mm at the center. A soft polymeric component, in one embodiment, for example, can have a thickness of about 2 mm at an edge and a thickness of about 5 mm at the center.

In some embodiments, the soft polymeric component has a width ranging from about 3 mm to about 20 mm, or from about 5 mm to about 100 mm. In other embodiments, the soft polymeric component has a width less than about 3 mm or greater than about 20 mm. In other embodiments, the soft polymeric component has a width less than about 5 mm or greater than about 100 mm. In some embodiments, the soft polymeric component has a length ranging from about 20 mm to about 100 mm. In some embodiments, the soft polymeric component has a length ranging from about 10 mm to about 50 mm. In other embodiments, the soft polymeric component has a length less than about 20 mm or greater than about 100 mm. In another embodiment, the soft polymeric component has a length less than about 10 mm or greater than about 50 mm.

Figure 6:
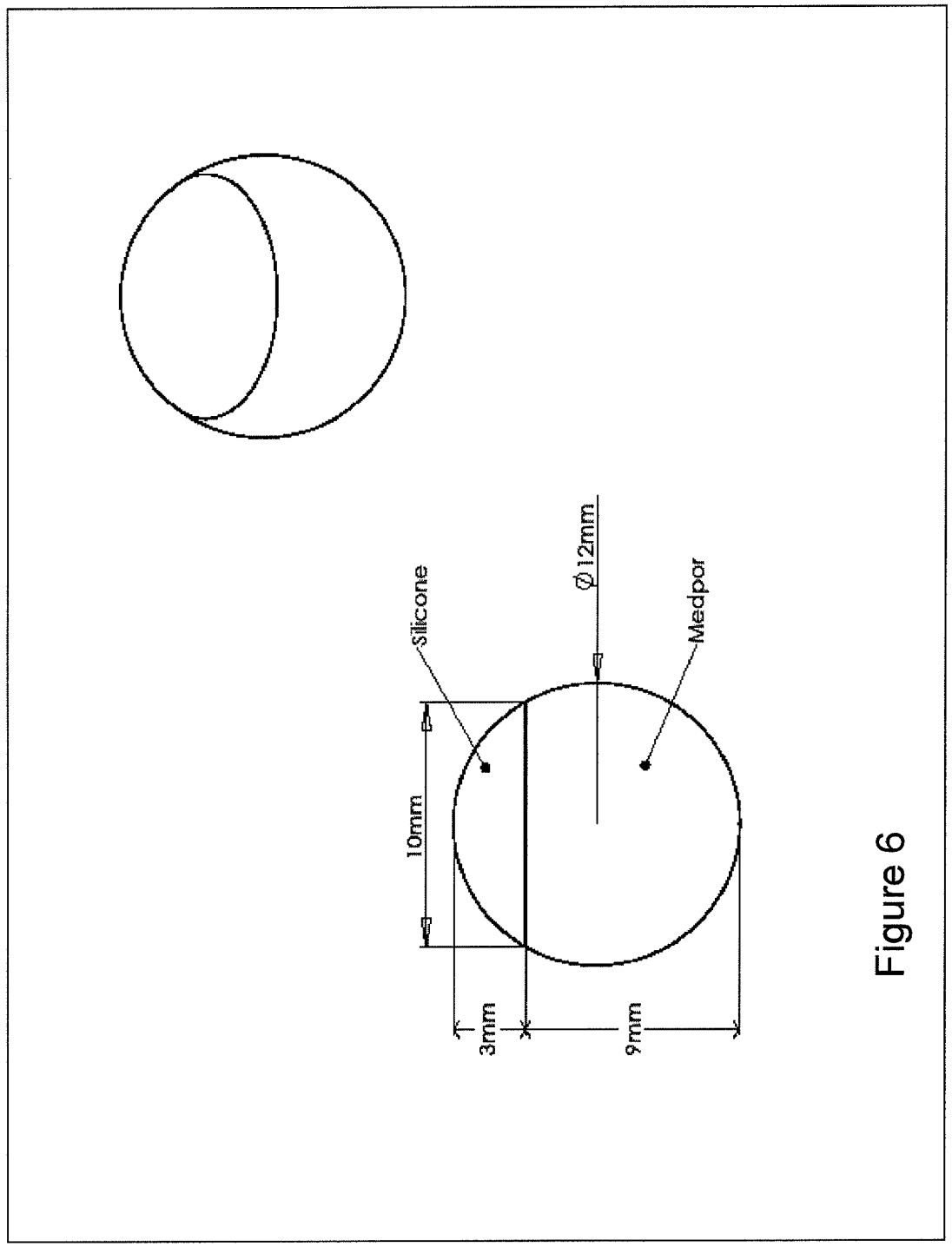
FIG. 6 illustrates an example of an eyeball implant according to the present invention.

In another embodiment, for example, an eyeball implant, the soft polymeric component can have a thickness of ranging from about 0.5 mm to about 10 mm, or from 2 mm to 5 mm. The concept is illustrated in FIG. 6.

In another embodiment composite implant can be in a sheet form. The soft polymeric component can have a thickness of ranging from about 0.2 mm to about 10 mm. In another embodiment, the soft polymeric component can have a thickness greater than about 10 mm or less than about 0.2 mm. Moreover, the thickness of the soft polymeric component can vary over the length and/or width of the soft polymeric component. Width and length will vary according to implant needs.

Porous Polymeric Substrate

In addition to a soft polymeric component, composite implants of the present invention comprise a porous polymeric substrate. A porous polymeric substrate, according to some embodiments of the present invention, facilitates cell migration and tissue growth into the porous polymeric substrate. The porous polymeric substrate, in some embodiments, demonstrates a porosity and pore structure operable to facilitate cell migration, vascular ingrowth and/or tissue ingrowth. In one embodiment, for example, a porous polymeric substrate facilitates osteoprogenitor cell migration, such as osteoblast migration into the composite implant for subsequent bone growth into and/or within the implant. Cellular and tissue ingrowth, as provided herein, can assist in stabilizing the composite implant thereby reducing tissue resorption at implant/host tissue interfaces.

The porous polymeric substrate, in some embodiments, comprises at least one porous polymeric layer. In other embodiments, the porous polymeric substrate comprises a plurality of porous polymeric layers. Polymers suitable for use in one or more layers of the porous substrate, in some embodiments, include polyolefins, polyesters, polyamides, polyketones such as polyetheretherketone, polyacrylates such as polymethacrylate and polymethylmethacrylate, or combinations thereof. In some embodiments, a polyolefin comprises polyethylene, polypropylene, and/or copolymers thereof. Polyethylene, in one embodiment, comprises high density polyethylene (HDPE). High density polyethylene, as used herein, refers to polyethylene having a density ranging from about 0.92 g/cm$^3$ to about 0.97 g/cm$^3$. In some embodiments, high density polyethylene has a degree of crystallinity ranging from about 50 to about 90. In another embodiment, polyethylene comprises ultrahigh molecular weight polyethylene (UHMWPE). Ultrahigh molecular weight polyethylene, as used herein, refers to polyethylene having a molecular weight greater than 1,000,000.

In some embodiments, the porous polymeric substrate further comprises ceramic and/or other biocompatible compositions in addition to polymers. In one embodiment, for example, the porous polymeric substrate further comprises particles of hydroxyapatite, bioglass, and/or titania or titanium dioxide disposed within at least one polymer layer of the substrate. In some embodiments, particles of hydroxyapatite, bioglass, and/or titania or titanium dioxide are dispersed throughout at least one polymer layer of the substrate. In some embodiments, the porous polymeric substrate further comprises a biocompatible mesh, such as titanium mesh as described in U.S. patent application Ser. No. 11/445,560, published as US 2006/0224242.

The porous polymeric substrate, in one embodiment, is sintered and comprises a plurality of polymeric particles. Polymeric particles for sintering can comprise any of the polymers described herein as being suitable for use in the porous substrate. Moreover, in some embodiments, ceramic and/or other biocompatible compositions such as hydroxyapatite, bioglass and/or titania particles or titanium dioxide can be mixed and cosintered with the polymeric particles in the production of a porous substrate.

The porous polymeric substrate, in some embodiments, comprises a compositional gradient. In one embodiment, for example, the porous polymeric substrate comprises a first layer of a first polymer and a second layer of a second polymer, wherein the first and second polymers are different. Embodiments of porous polymeric substrates of the present invention contemplate any number of layers of different polymers arranged in any order. Additionally, in some embodiments, sintered polymeric layers can be arranged with non-sintered polymeric layers in any order.

Compositional gradients permit tailoring of the porous polymeric substrate to meet the requirements of specific applications. In one embodiment, for example, the porous polymeric substrate comprises a first polymeric layer for facilitating cellular and tissue ingrowth and a second layer for coupling to the soft polymeric layer. In facilitating cellular and tissue ingrowth, the first layer comprises a polymer most compatible with the host tissue. A polymer most compatible with host tissue, however, may not be the most compatible for coupling to the soft polymeric component or an intervening adhesive layer. As a result, the second layer can be selected to comprise a polymer most compatible for coupling to the soft polymeric component.

In one embodiment, the porous polymeric substrate has an average pore size ranging from about 1 μm to about 1 mm. In another embodiment, the porous polymeric substrate has an average pore size ranging from about 10 μm to about 500 μm or from about 100 μm to about 300 μm. In some embodiments, the porous polymeric substrate has an average pore size ranging from about 25 μm to about 100 μm.

The porous polymeric substrate, in some embodiments, has a porosity ranging from about 10% to about 90%. In other embodiments, the porous polymeric substrate has a porosity ranging from about 20% to about 80%, from about 30% to about 70%, or from about 40% to about 60%. In one embodiment, the porous polymeric substrate has a porosity of about 50%. In some embodiments, the porous polymeric substrate has a porosity less than about 10% or greater than about 90%.

In some embodiments, the porous polymeric substrate has a porosity gradient. In one embodiment, the porous polymeric substrate of a composite implant comprises a region proximate the soft polymeric component and a region distal to the soft polymeric component, wherein the region proximate the soft polymeric component has a porosity less than the region distal to the soft polymeric component. Such an arrangement permits the porous polymeric substrate to provide a porosity and pore structure suitable for allowing cell migration and tissue growth into the substrate while retaining a less porous surface increasing the contact area with the soft polymeric component.

In some embodiments, the porous polymeric substrate is rigid. In other embodiments, the porous polymeric substrate is flexible and/or foldable. Moreover, in some embodiments, the porous polymeric substrate has a Shore D hardness greater than about 30. In another embodiment, the porous polymeric substrate has a Shore D hardness of at least 50. In one embodiment, the porous polymeric substrate has a Shore D of at least 60. In some embodiments, the porous polymeric substrate has a Shore D hardness ranging from about 40 to about 70. In some embodiments, the porous polymeric substrate is soft and can demonstrate mechanical properties consistent with soft, non-load bearing or load bearing tissues of a mammalian body as provided herein. In such embodiments, the porous polymeric substrate can comprise polymers consistent with those provided for the soft polymeric component. In some embodiments, the porous polymeric substrate has a Shore A hardness of greater than about 20. In some embodiments, the porous polymeric substrate has a Shore A hardness of greater than about 30. In other embodiments, the porous polymeric substrate has a Shore A hardness of less than about 80. Hardness of the porous polymeric substrate can be determined according to ASTM D2240.

The porous polymeric substrate of a composite implant can have any desired length, width, and thickness. The length, width, and thickness of the porous polymeric substrate can depend on the dimensions of the implant site and/or the application of the implant such as craniofacial applications. In one embodiment, for example, a chin implant (FIG. 5), the porous polymeric substrate has a thickness ranging from about 0.2 mm to about 10 mm. In another embodiment, the porous polymeric substrate has a thickness ranging from about 0.5 mm to about 5 mm or from a 0.1 mm to about 1 mm.

In another embodiment, for example, an eyeball implant, the porous polymeric substrate has a thickness from 5 mm to 25 mm. The depth of the cut has a range from 1 mm to 10 mm. The depth of the cut refers to the thickness of the cut from a sphere of porous polymeric substrate which is occupied by the soft polymeric component. For example, in FIG. 6, the depth of the cut is 3 mm of the 12 mm diameter of the sphere and is comprised of silicone.

In another embodiment, a sheet form of a craniofacial implant, the thickness of the porous polymeric substrate has a range from 0.2 mm to 10 mm, or from 0.5 mm to 5 mm. Sheet forms of other implants may have thicknesses of porous polymeric substrate with a range from 0.2 mm to 50 mm, or from 0.5 mm to 25 mm, or from 1.0 mm to 10 mm, or any value within these ranges.

In some embodiments, the porous polymeric substrate further comprises at least one non-porous barrier layer. The non-porous barrier layer, in some embodiments, is disposed proximate the interface with the soft polymeric component. In being proximate to the interface with the soft polymeric component, the non-porous barrier layer, in some embodiments, can limit or restrict the depth to which the soft polymeric component penetrates the pores of the polymeric substrate.

In some embodiments, a non-porous barrier layer is disposed distal to the interface with the soft polymeric component. In one embodiment, for example, a non-porous barrier layer is disposed on a surface of the porous polymeric substrate operable to support cellular and tissue ingrowth.

In disposing a non-porous barrier layer on a surface of the porous polymeric substrate operable to support cellular and tissue ingrowth, cellular and tissue ingrowth can be patterned or guided into the porous polymeric substrate. In one embodiment, for example, a non-porous barrier layer covers the central region of a porous surface of the polymeric substrate leaving the periphery of the porous surface available for supporting cellular and tissue ingrowth. A non-porous barrier layer can be provided in any desired pattern on a surface of the porous polymeric substrate operable to support cellular and tissue ingrowth.

In some embodiments, a porous polymeric substrate comprises a plurality of non-porous barrier layers. In one embodiment, a porous polymeric substrate comprises a first non-porous barrier layer proximate to the interface with the soft polymeric component and a second non-porous barrier layer distal to the interface with the soft polymeric component.

A non-porous barrier layer, in some embodiments, comprises a polymeric material consistent with that of the porous polymeric substrate. In a specific embodiment, the non-porous barrier material is HDPE. In other embodiments, a non-porous barrier layer comprises a polymeric material different than that of the porous polymeric substrate. In some embodiments, a non-porous barrier layer comprises polyolefins, polyesters, polyamides, polyketones such as polyetheretherketone, polyacrylates such as polymethacrylate and polymethylmethacrylate, thermoplastic resins, or combinations thereof. In some embodiments, a polyolefin comprises polyethylene, polypropylene, and/or copolymers thereof. In some embodiments, a non-porous barrier layer comprises hydroxyapatite, ceramics, such as bioglass and metal oxides including titania, titanium dioxide or mixtures thereof. In some embodiments, a non-porous barrier layer comprises any biocompatible material suitable for long-term implantation.

In some embodiments, the non-porous barrier layer has a thickness from 0.05 mm to 2 mm. In some embodiments, non-porous barrier layers are less than 0.05 mm or greater than 2 mm.

In some embodiments, the porous polymeric substrate is coextensive or substantially coextensive with the soft polymeric component. In other embodiments, the porous polymeric substrate is not coextensive with the soft polymeric component. In one embodiment, for example, the porous polymeric substrate is only located around the perimeter of the soft polymeric component.

In embodiments wherein the porous polymeric substrate is not coextensive with the soft polymeric component, the soft polymeric component has a surface area greater than the porous polymeric substrate. Alternatively, in other embodiments, the porous polymeric substrate has a surface area greater than the soft polymeric component.

A composite implant, according to some embodiments of the present invention, can be any physical shape, such as spherical, elliptical, sheet, disk, conical, or another shape.

Coupling the Soft Polymeric Component to the Porous Polymeric Substrate

The soft polymeric component can be coupled to the porous polymeric substrate using a variety of methods, including but not limited to chemical and mechanical means.

Figure 7:
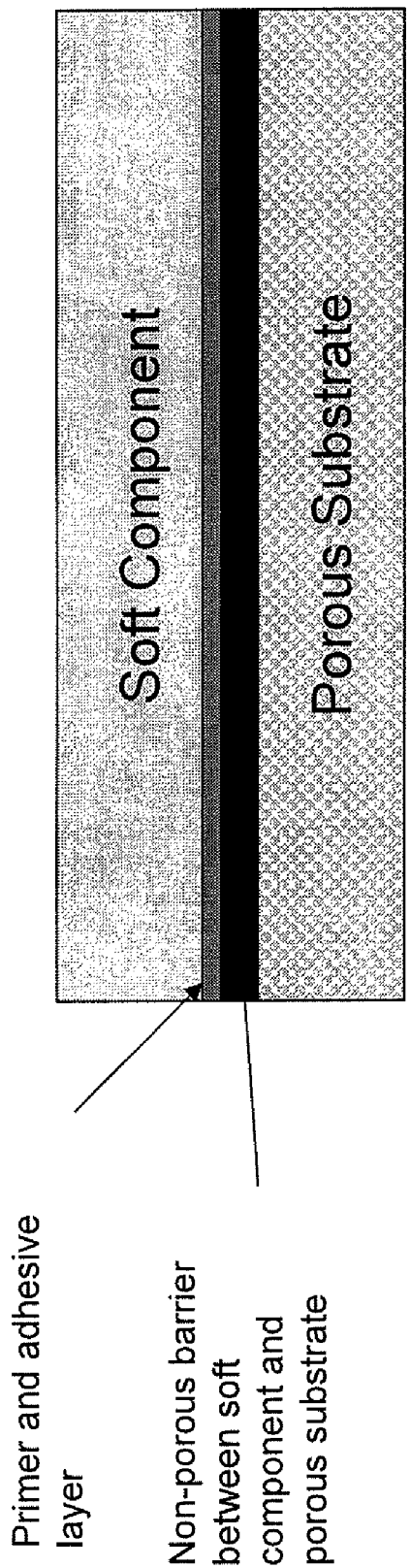
FIG. 7 illustrates an sheet implant according to one embodiment of the present invention with the soft component coupled to the porous substrate with adhesive and a non-porous barrier layer between the soft component and the porous substrate.

A composite implant, according to some embodiments of the present invention, further comprises an adhesive component operable to couple the soft polymeric component to the porous polymeric substrate (FIG. 7). In some embodiments, the adhesive component comprises at least one layer of a biocompatible adhesive. In some embodiments, a biocompatible adhesive comprises a silicone. In some embodiments, a silicone comprises a silicone gel, silicone elastomer, or combinations thereof. FIG. 7 illustrates that a soft component is coupled to a porous substrate having a non-porous barrier with adhesive.

In some embodiments, the adhesive component comprises a compositional gradient. In one embodiment, an adhesive component comprises a first layer of a first adhesive and a second layer of a second adhesive, wherein the first and second adhesives are different. In some embodiments, the first adhesive is selected to form favorable interactions with the soft polymeric component while the second adhesive is selected to form favorable interactions with the porous polymeric substrate.

Figure 8:
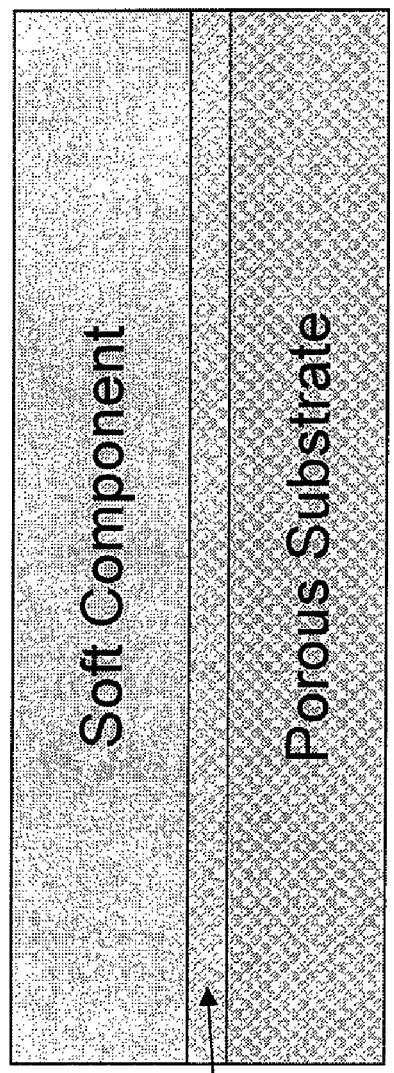
FIG. 8 illustrates a sheet implant according to one embodiment of the present invention with the soft component partially penetrated into the porous substrate.

In some embodiments, the soft polymeric component is coupled to the porous polymeric substrate by mechanical engagement wherein the soft polymeric component at least partially penetrates a plurality of pores of the polymeric substrate (FIG. 8). In penetrating the pores of the polymeric substrate, according to some embodiments of the present invention, the soft polymeric component is not completely absorbed by the porous polymeric substrate. Moreover, as provided herein, the porous polymeric substrate, in some embodiments, further comprises a barrier layer proximate to the interface with the soft polymeric component which is operable to restrict the penetration of the soft polymeric component into the porous polymeric substrate.

Figure 9:
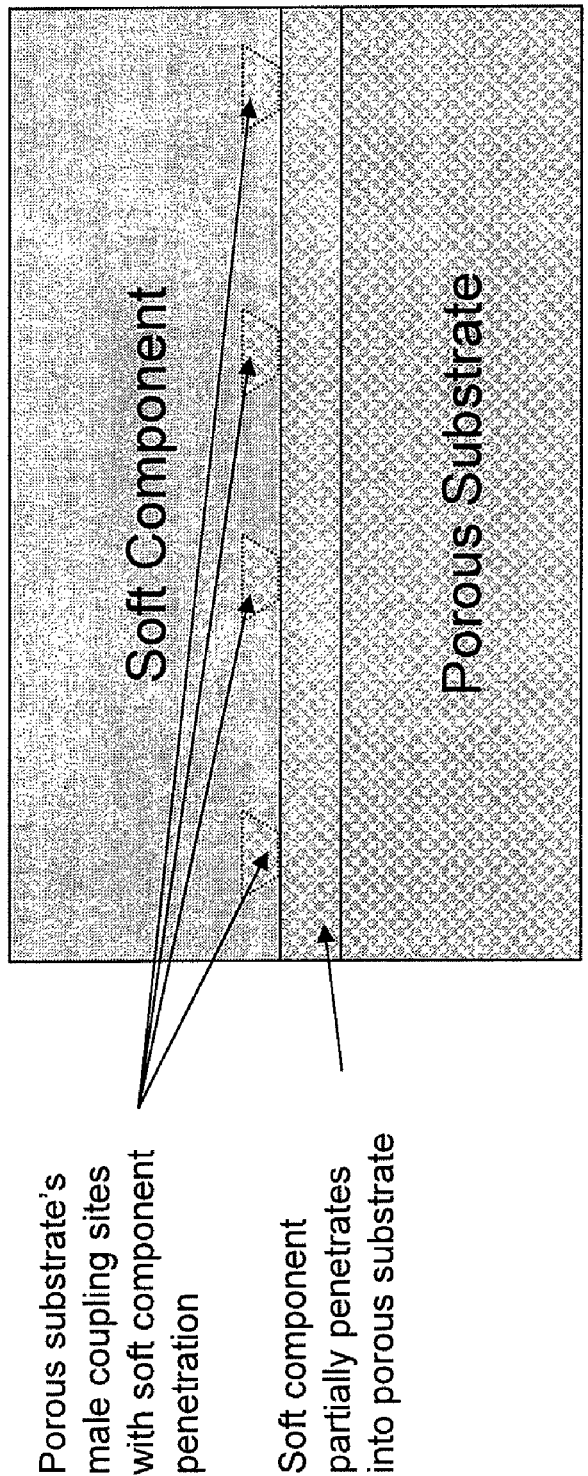
FIG. 9 illustrates an implant according to one embodiment of the present invention. The porous substrate has male coupling sites with the soft component penetrating into the male coupling sites and partially penetrating into the porous substrate.

In some embodiments, the porous substrate has male coupling sites and the soft polymeric component is coupled to the porous polymeric substrate by mechanical engagement wherein the soft polymeric component at least partially penetrates a plurality of pores of the polymeric substrate and its male coupling sites. In a specific embodiment, the soft polymeric component at least partially penetrates pores of the polymeric substrate by being formed in a mold comprising the polymeric substrate with the male coupling sites (FIG. 9). In another embodiment, the soft polymeric component may be preformed with corresponding female coupling sites and coupled to porous substrate by applying adhesives. The male coupling sites of the porous substrate may have the same or different sizes or shapes and they may be less or equal to the thickness of the soft polymeric component of the composite implant. Male/female physical coupling provides improved interfacial strength between the soft polymeric component and the porous polymeric substrate in the composite implant.

Figure 10:
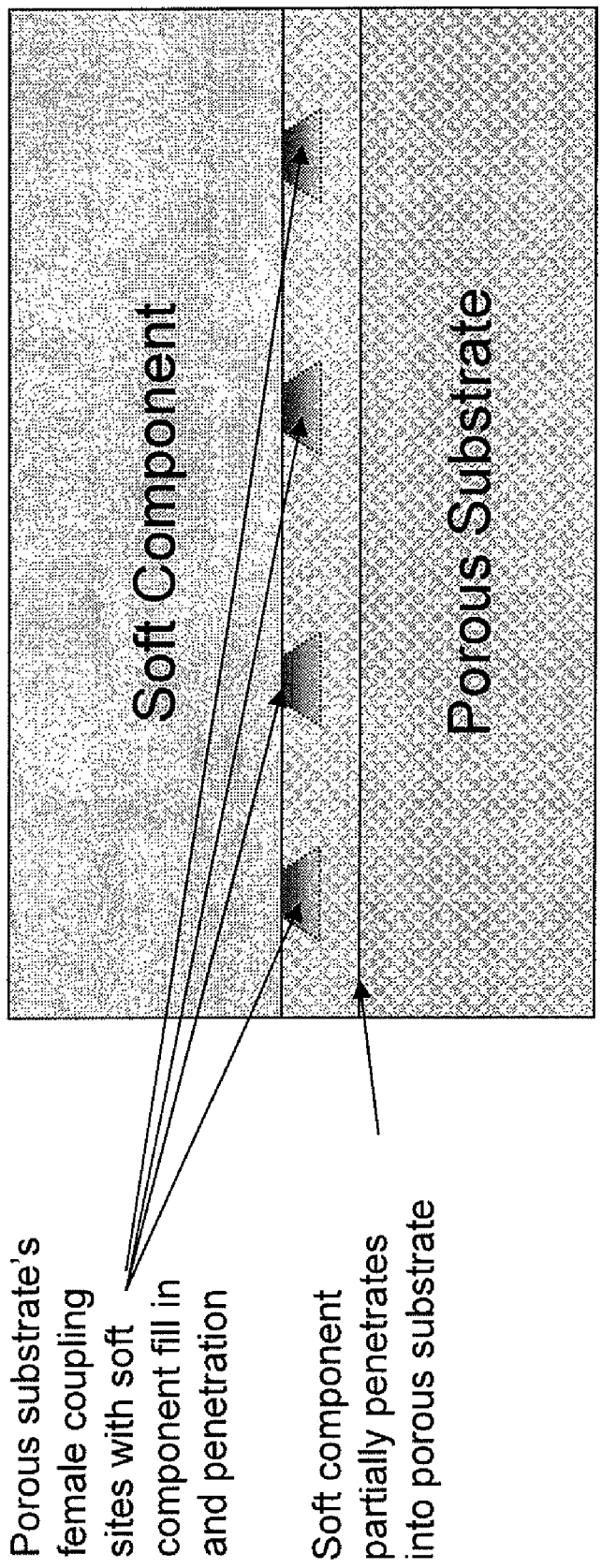
FIG. 10 illustrates an implant according to one embodiment of the present invention. The porous substrate has female coupling sites with the soft component, the soft component filling into the female coupling sites and partially penetrating into the porous substrate.

In some embodiments, the porous polymeric substrate has female coupling sites and the soft polymeric component is coupled to the porous polymeric substrate by mechanical engagement wherein the soft polymeric component at least partially penetrates a plurality of pores of the polymeric substrate and its female coupling sites. In a specific embodiment, the soft polymeric component at least partially penetrates pores of the polymeric substrate by being formed in a mold comprising the polymeric substrate with the female coupling sites (FIG. 10). In another embodiment, the soft polymeric component may be preformed with corresponding male coupling sites and coupled to the porous polymeric substrate by applying adhesive. The female coupling sites of the porous polymeric substrate may have the same or different sizes or shapes and they may be less or equal to the thickness of the porous polymeric substrate of the composite implant. Male/female physical coupling provides improved interfacial strength between the soft polymeric component and the porous polymeric substrate in the composite implant.

Figure 11:
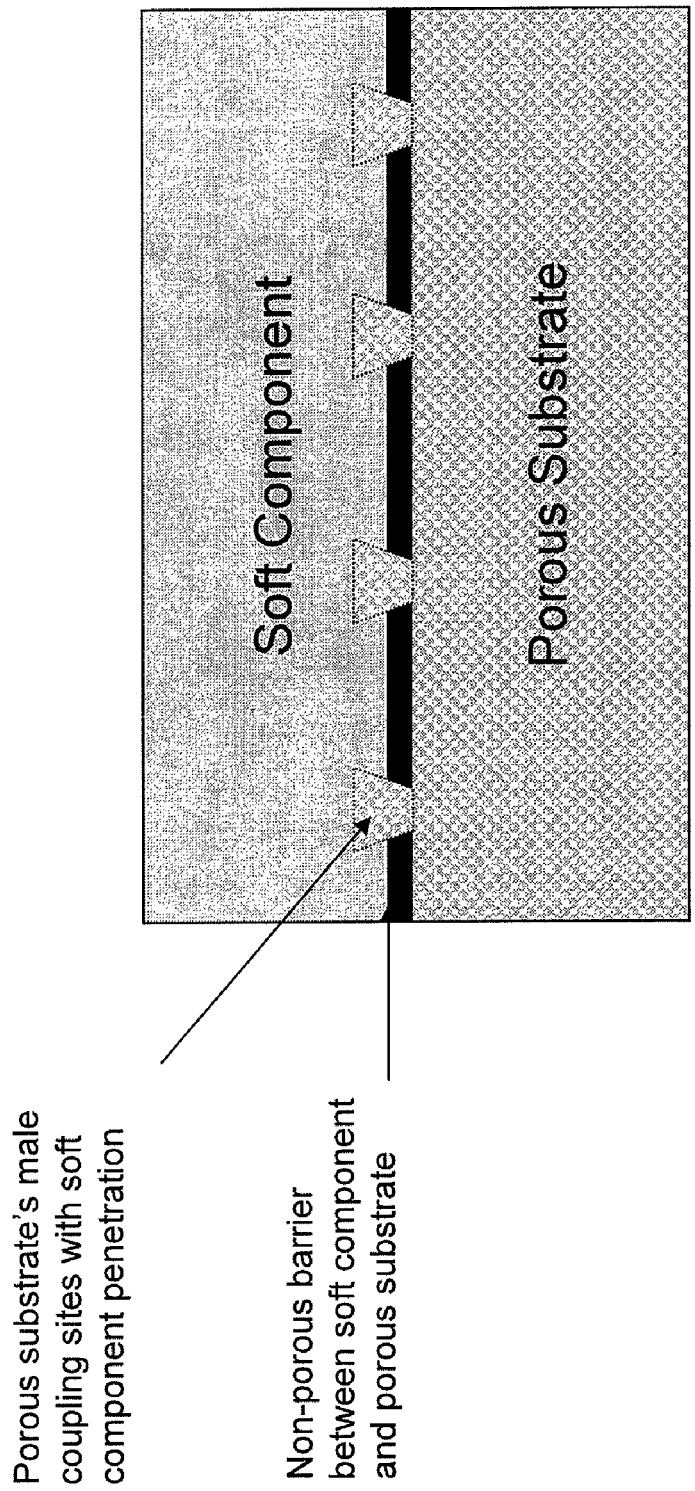
FIG. 11 illustrates an implant according one to embodiment of the present invention. The porous substrate has discrete male coupling sites with the soft component penetrating into the male coupling sites. A non-porous barrier layer is located between the soft component and the porous substrate at locations surrounding the male coupling sites.

In some embodiments, the porous substrate with male coupling sites comprises one or more non-porous barrier layers (FIG. 11). The soft polymeric component is coupled to the porous polymeric substrate by mechanical engagement wherein the soft polymeric component at least partially penetrates a plurality of pores of male coupling sites of the polymeric substrate. In some embodiments, the soft polymeric component with corresponding female coupling sites is coupled to the porous substrate by applying adhesive. The male coupling sites of the porous substrate may have the same or different sizes or shapes and they may be less or equal to the thickness of the soft polymeric component of the composite implant. Male/female physical coupling provides improved interfacial strength between the soft polymeric component and the porous polymeric substrate in the composite implant.

Figure 12:
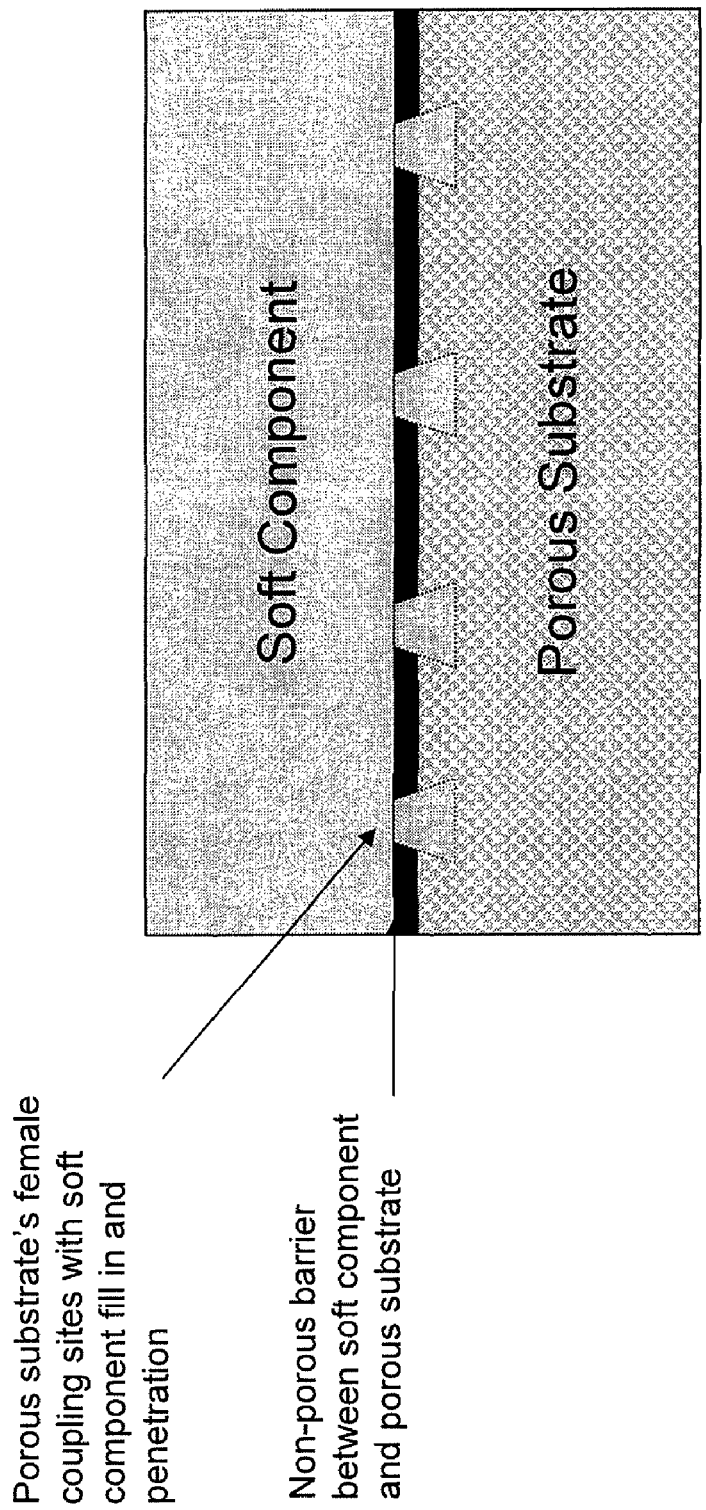
FIG. 12 illustrates an implant according to one embodiment of the present invention. The porous substrate has female coupling sites with the soft component. The soft component fills into the female coupling sites. The porous substrate has a non-porous barrier layer between it and the soft component except at the locations of the female coupling sites.

In some embodiments, the porous substrate with female coupling sites comprises one or more non-porous barrier layers. The soft polymeric component is coupled to the porous polymeric substrate by mechanical engagement wherein the soft polymeric component fills in the porous substrate's female coupling sites and at least partially penetrates a plurality of pores of the female coupling sites of the porous polymeric substrate (FIG. 12 provides an example). In some embodiments, the soft polymeric component with corresponding male coupling sites of the porous polymeric substrate is coupled to the porous polymeric substrate by applying adhesive. The female coupling sites of the porous polymeric substrate may have the same or different sizes or shapes and they may be less or equal to the thickness of the porous polymeric substrate of the composite implant. Male/female physical coupling provides improved interfacial strength between the soft polymeric component and the porous polymeric substrate in the composite implant.

Figure 13:
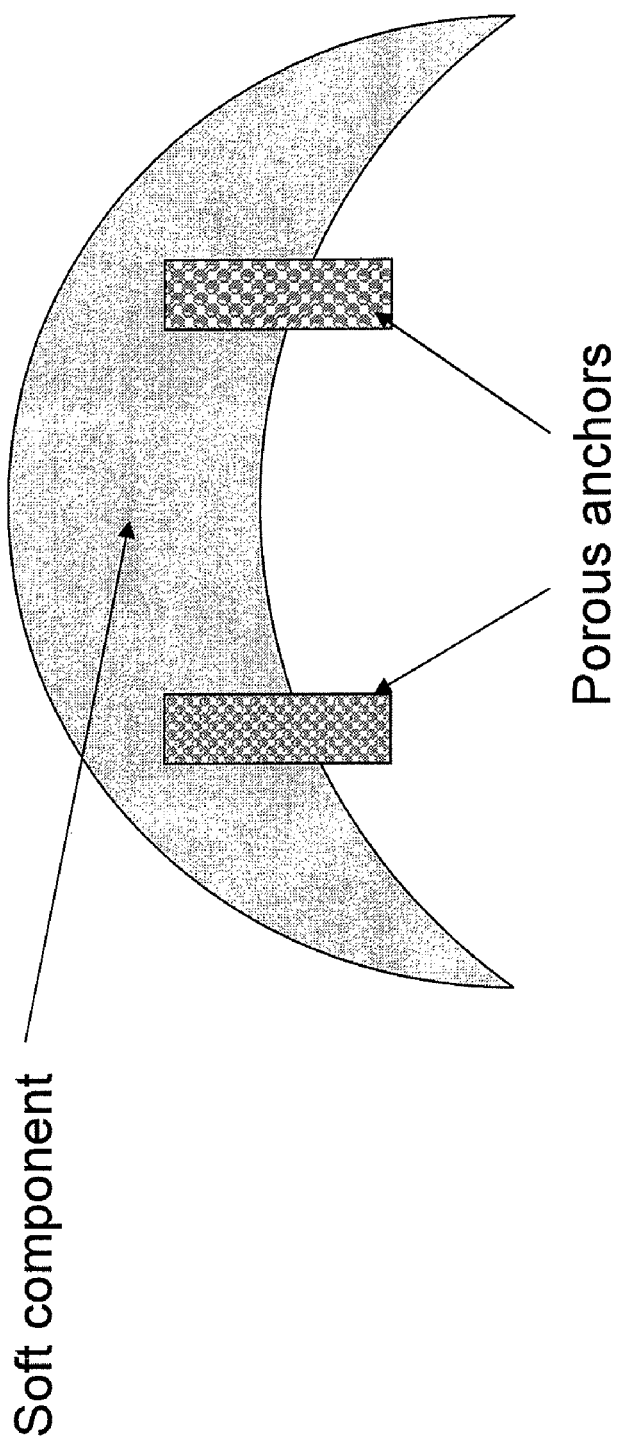
FIG. 13 illustrates a composite implant according to one embodiment of the present invention with porous anchors of the polymeric substrate penetrating into the soft component.

In some embodiments, the porous substrate in the composite implant is discrete and functions as anchors. The porous substrates, labeled as porous anchors in FIG. 13, can be any size or shape and partially imbedded in the soft polymeric component. The soft polymeric component is coupled to the porous polymeric substrate by mechanical engagement wherein the soft polymeric component at least partially penetrates a plurality of pores of the porous substrates. This design provides strong coupling between the soft polymeric component and porous substrate(s); maintains the flexibility of the soft component and provides anchor sites for cellular and tissue ingrowth.

In some embodiments, the porous substrate and soft polymeric component are coupled together by screws, such as metal screws. The composite implant may be made by screwing together the pre-molded soft component and the porous substrate. Alternatively, the screw can be pre-molded into the soft component or into the porous polymeric substrate.

In some embodiments, the porous substrate and soft polymeric component are coupled together by bolts and nuts. The composite implant may be made by coupling together the pre-molded soft component and the porous substrate with bolts and nuts. In an specific embodiment, the bolt and nut are molded in the soft component and the porous substrate separately.

In some embodiments, the soft polymeric component at least partially penetrates pores of the porous polymeric substrate by being formed in a mold comprising the porous polymeric substrate. In one embodiment, for example, a soft polymeric component comprising a poly(vinyl alcohol) hydrogel is disposed in a mold containing a porous polymeric substrate. The poly(vinyl alcohol) hydrogel at least partially penetrates the pores of the porous polymeric substrate and is subsequently subjected to the desired number of freeze-thaw cycles to complete production of the composite implant.

In another embodiment, the soft polymeric component comprises a polysiloxane which is prepared and applied to a porous polymeric substrate. The polysiloxane at least partially penetrates pores of the polymeric substrate and is subsequently cured (cross-linked) to complete production of the composite implant. In some embodiments, the soft polymeric component at least partially penetrates pores of the polymeric substrate by the application of pressure to the soft polymeric component. The application of pressure to the soft polymeric component forces at least a portion of the soft polymeric component into pores of the polymeric substrate.

In some embodiments, a composite implant of the present invention further comprises one or a plurality of bioactive agents. Bioactive agents may promote or facilitate cell migration and tissue growth into the composite implant. In some embodiments, bioactive agents for use in composite implants of the present invention comprise heparin, matrix inhibitors, antibodies, cytokines, integrins, thrombins, thrombin inhibitors, proteases, anticoagulants, antibiotics, glycosaminoglycans, collagen crosslinking inhibitors such as β-aminopropionitrile and cis-4-hydroxyproline, or growth factors such as such as fibroblast growth factors (FGFs), epidermal growth factors (EGFs), transforming growth factors (TGFs), keratinocyte growth factors (KGFs), insulin-like growth factors (IGFs), bone morphogenetic proteins (BMPs), platelet derived growth factors (PDGFs) or combinations thereof.

Bioactive agents, in some embodiments, are disposed on surfaces of the composite implant. In other embodiments, bioactive agents are disposed within porous regions of the implant such as the porous polymeric substrate. Bioactive agents can be disposed within the soft polymeric component in some embodiments wherein the soft polymeric component is porous.

Method of Making a Composite Implant

In another aspect, the present invention provides methods of making composite implants. In one embodiment, a method of making a composite implant comprises providing a soft polymeric component, providing a porous polymeric substrate, and coupling the soft polymeric component to the porous polymeric substrate. Moreover, coupling the soft polymeric component to the porous polymeric substrate, in some embodiments, comprises penetrating a plurality of pores of the porous polymeric substrate with the soft polymeric component. In one embodiment, the method of making a composite implant comprises applying a liquid form of a polymer or its solution in the cavity of a mold with a pre-formed porous polymeric substrate and contacting the porous polymeric substrate with the liquid form of the polymer or its solution. The liquid form polymer or its solution is sequentially cured/cross-linked and solidified in the mold. The soft polymer component is solidified inside the portion of the pores of the porous polymeric substrate and forms a strong mechanical coupling. In other embodiments, coupling the soft polymeric component to the porous polymeric substrate comprises providing an adhesive component and interposing the adhesive component between the pre-formed soft polymeric component and the pre-formed porous polymeric substrate.

In another aspect, the present invention provides methods of producing a composite implant comprising a soft polymeric component and a porous polymeric substrate. In one embodiment, a method of producing a composite implant comprises providing a soft polymeric component, providing a porous polymeric substrate, and coupling the soft polymeric component to the porous polymeric substrate. In some embodiments, providing a porous polymeric substrate comprises providing a plurality of polymeric particles and sintering the plurality of polymeric particles. Moreover, coupling the soft polymeric component to the porous polymeric substrate, in some embodiments, comprises at least partially penetrating a plurality of pores of the porous polymeric substrate with the soft polymeric component. In other embodiments, coupling the soft polymeric component to the porous polymeric substrate comprises providing an adhesive component and interposing the adhesive component between the soft polymeric component and the porous polymeric substrate.

In another embodiment, a method of producing a composite implant comprises filling the mold with a liquid form of the soft polymeric component, adding a preformed porous polymeric component and having part of the porous polymeric component contacted to or inserted into the soft polymeric component, and curing and solidifying the soft polymeric component to the porous polymeric component. In one embodiment, curing and solidifying is a freeze and thaw process. In another embodiment, curing and solidifying is a heating process. In some embodiments, providing a porous polymeric component comprises providing a plurality of polymeric particles and sintering the plurality of polymeric particles. Moreover, coupling the soft polymeric component to the porous polymeric component, in some embodiments, comprises at least partially penetrating a plurality of pores of the porous polymeric substrate with the soft polymeric component.

In another embodiment, a method of producing a composite implant comprises filling the bottom part of a cavity of a mold with a liquid form soft polymeric component, adding polymer particles on the top of the liquid form soft polymeric component in the cavity and filling the mold cavity, closing the mold cavity, heating the mold in an oven or a hot press, curing and solidifying the soft polymeric component, sintering polymer particles into a porous substrate and coupling the soft polymeric component to the porous polymeric substrate simultaneously in the mold cavity. In some embodiments, the soft polymeric component at least partially penetrates a plurality of pores of the porous polymeric substrate.

In some embodiments, providing a soft polymeric component comprises providing a poly(vinyl alcohol) hydrogel. Poly(vinyl alcohol) hydrogels, in some embodiments, are produced by freeze-thaw procedures. In one embodiment, poly(vinyl alcohol) hydrogels for use in soft polymeric components of the present invention are produced according to the methods described in U.S. Pat. No. 6,268,405.

Moreover, in some embodiments, providing a soft polymeric component comprises providing a silicone layer. A silicone layer, in some embodiments, is produced by forming a silicone gel. In other embodiments, a silicone layer is produced by forming a silicone elastomer. In a further embodiment, a silicone layer is produced by combining a silicone gel and a silicone elastomer.

In some embodiments, providing a porous polymeric substrate comprises providing a HDPE or UHMWPE, either in a pre-molded form before contact with the soft polymeric component, or as particles which may contact the soft polymeric component before sintering.

Method of Treating a Patient with a Composite Implant

In a further aspect, the present invention provides methods of treating a patient in need of an implant. In one embodiment, a method of treating a patient in need of an implant comprises providing an implant comprising a soft polymeric component coupled to a porous polymeric substrate, providing access to an implant site, and inserting the implant into an implant site of the patient. In some embodiments, the implant is folded before insertion into the implant site. In some embodiments, providing access to an implant site comprises making an incision to expose the implant site. In some embodiments, a method of treating a patient in need of an implant further comprises unfolding the composite implant in the implant site. In some embodiments, a method of treating a patient in need of an implant further comprises disposing the porous polymeric substrate of the composite implant adjacent to bone in the implant site and subsequently growing bone into the porous polymeric substrate The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Silicone and MEDPOR® Composite Implant

A composite implant comprising a soft silicone (polysiloxane) component and a porous HDPE substrate (MEDPOR®) was produced according to the following procedure. MED-4244 was obtained from NuSil Technology of Carpinteria, Calif. Part A and Part B of MED-4244 were mixed in container in a 10:1 ratio of Part A to Part B in accordance with the product instructions. A vacuum was applied to the mixture to remove any air bubbles. 7 grams of the silicone mixture were poured into the cavity of an aluminum chin mold. A MEDPOR® substrate was obtained from Porex Surgical, Inc. of Newnan, Ga. The MEDPOR® substrate displayed a crescent shape with a radius of 35 mm and a uniform thickness of 2 mm. The substrate additionally displayed a length of 65 mm and width of 15 mm in the center, which tapered down to 3 mm on each end. The MEDPOR® substrate had an average pore size greater than about 100 µm and a porosity of about 50%. The MEDPOR® substrate was affixed to the core of the mold, and the core was inserted into the mold cavity containing the silicone mixture. When the core was inserted into the cavity of the mold, the silicone mixture and MEDPOR® substrate were placed into contact.

The mold was subsequently placed in a hot press at 177° C. for five minutes to cure the silicon mixture. The mold was removed from the oven and allowed to cool to room temperature. The mold was disassembled, and the composite implant comprising a soft silicone component and a porous HDPE substrate was removed. The composite implant was future cured at 150° C. for about 1 hour in an oven for completed cure.

EXAMPLE 2

Poly(vinyl alcohol) (PVA) and MEDPOR® Composite Implant

A composite implant comprising a soft poly(vinyl alcohol) hydrogel component and a porous HDPE substrate (MEDPOR®) was produced according to the following procedure. Poly(vinyl alcohol) powder was mixed with water in a ratio of 20 parts powder to 80 parts water. The resulting mixture was placed in an oven at 105° C. for 16 hours. The poly(vinyl alcohol)/water mixture was removed from the oven, and 8 g of the mixture was poured into the cavity of an aluminum chin mold.

A MEDPOR® substrate was obtained from Porex Surgical, Inc. of Newnan, Ga. The MEDPOR® substrate displayed a crescent shape with a radius of 35 mm and a uniform thickness of 2 mm. The substrate additionally displayed a length of 65 mm and width of 15 mm in the center, which tapered down to 3 mm on each end. The MEDPOR® substrate had an average pore size greater than about 100 µm and a porosity of about 50%. The MEDPOR® substrate was affixed to the core of the mold, and the core was inserted into the mold cavity containing the poly(vinyl alcohol)/water mixture. When the core was inserted into the cavity of the mold, the poly (vinyl alcohol)/water mixture and MEDPOR® substrate were placed into contact.

The mold was placed into a freezer at −20° C. for 16 hours. The mold was subsequently removed from the freezer and allowed to thaw at room temperature. The foregoing freeze/thaw cycle was repeated five times. The mold was disassembled, and the composite implant comprising a soft poly (vinyl alcohol) hydrogel component and a porous HDPE substrate was removed from the mold. The implant may be additionally cross-linked by application of freeze/thaw cycles.

EXAMPLE 3

Silicone and MEDPOR® Composite Implant for a Chin

A composite implant comprising a soft silicone (polysiloxane) component and a porous HDPE substrate was produced according to the following procedure. MED-4244 was obtained from NuSil Technology of Carpinteria, Calif. Part A and Part B of MED-4244 were mixed in container in a 10:1 ratio of Part A to Part B in accordance with the product instructions. A vacuum was applied to the mixture to remove any air bubbles. 7 grams of the silicone mixture were poured into the cavity of an aluminum chin mold. The mold was subsequently placed in a hot press at 177° C. for five minutes to cure the silicon mixture. The mold was removed from the oven and allowed to cool to room temperature. The mold was disassembled, and a soft silicone component was removed and was later cured at 150° C. for about 1 hour in an oven for a completed cure.

A MEDPOR® substrate was obtained from Porex Surgical, Inc. of Newnan, Ga. The MEDPOR® substrate displayed a crescent shape with a radius of 35 mm and a uniform thickness of 2 mm. The substrate additionally displayed a length of 65 mm and width of 15 mm in the center, which tapered down to 3 mm on each end. The MEDPOR® substrate had an average pore size greater than about 100 µm and a porosity of about 50%. The MEDPOR® substrate was affixed to the soft silicone component by applying a silicone based primer and an adhesive. The composite implant was then cured at 150° C. for 15 minutes or at room temperature for at least a day.

EXAMPLE 4

Silicone and MEDPOR® Composite Implant with a Non-Porous Barrier for a Chin

A composite implant comprising a soft silicone (polysiloxane) component and a porous HDPE substrate was produced according to the following procedure. MED-4244 was obtained from NuSil Technology of Carpinteria, Calif. Part A and Part B of MED-4244 were mixed in container in a 10:1 ratio of Part A to Part B in accordance with the product instructions. A vacuum was applied to the mixture to remove any air bubbles. 7 grams of the silicone mixture were poured into the cavity of an aluminum chin mold. The mold was subsequently placed in a hot press at 177° C. for five minutes to cure the silicon mixture. The mold was removed from the oven and allowed to cool to room temperature. The mold was disassembled, and a soft silicone component was removed and was later cured at 150° C. for about 1 hour in an oven for a completed cure.

A MEDPOR® substrate was obtained from Porex Surgical, Inc. of Newnan, Ga. The MEDPOR® substrate displayed a crescent shape with a radius of 35 mm and a uniform thickness of 2 mm. The substrate additionally displayed a length of 65 mm and width of 15 mm in the center, which tapered down to 3 mm on each end. The MEDPOR® substrate had an average pore size greater than about 100 µm and a porosity of about 50% on one surface. The other surface was solid and non-porous. The MEDPOR® substrate was affixed to the soft silicone component by applying a silicone based primer and an adhesive to the MEDPOR® non-porous side surface and cured. The composite implant was then cured at 150° C. for 15 minutes or at room temperature for at least a day.

EXAMPLE 5

PVA and MEDPOR® Composite Implant for a Chin

A composite implant comprising a soft poly(vinyl alcohol) hydrogel component and a porous HDPE substrate was produced according to the following procedure. Poly(vinyl alcohol) powder was mixed with water in a ratio of 20 parts powder to 80 parts water. The resulting mixture was placed in an oven at 105° C. for 16 hours. The poly(vinyl alcohol)/water mixture was removed from the oven, and 8 g of the mixture was poured into the cavity of an aluminum chin mold. The mold was placed into a freezer at −20° C. for 16 hours. The mold was subsequently removed from the freezer and allowed to thaw at room temperatures. The foregoing freeze/thaw cycle was repeated five times. The mold was disassembled, and a soft poly(vinyl alcohol) hydrogel component was removed from the mold.

A MEDPOR® substrate was obtained from Porex Surgical, Inc. of Newnan, Ga. The MEDPOR® substrate displayed a crescent shape with a radius of 35 mm and a uniform thickness of 2 mm. The substrate additionally displayed a length of 65 mm and width of 15 mm in the center, which tapered down to 3 mm on each end. The MEDPOR® substrate had an average pore size greater than about 100 µm and a porosity of about 50%. The MEDPOR® substrate was affixed to the soft PVA component by applying silicone based primer and an adhesive. The composite implant was then cured at room temperature for at least a day.

EXAMPLE 6

PVA and MEDPOR® Composite Implant with a Non-Porous Barrier

A composite implant comprising a soft poly(vinyl alcohol) hydrogel component and a porous HDPE substrate is produced according to the following procedure. Poly(vinyl alcohol) powder is mixed with water in a ratio of 20 parts powder to 80 parts water. The resulting mixture is placed in an oven at 105° C. for 16 hours. The poly(vinyl alcohol)/water mixture is removed from the oven, and 8 g of the mixture is poured into the cavity of an aluminum chin mold. The mold is placed into a freezer at −20° C. for 16 hours. The mold is subsequently removed from the freezer and allowed to thaw at room temperature. The foregoing freeze/thaw cycle is repeated five times. The mold is disassembled, and a soft poly(vinyl alcohol) hydrogel component is removed from the mold.

A MEDPOR® substrate is obtained from Porex Surgical, Inc. of Newnan, Ga. The MEDPOR® substrate displays a crescent shape with a radius of 35 mm and a uniform thickness of 2 mm. The substrate additionally displays a length of 65 mm and width of 15 mm in the center, which tapers down to 3 mm on each end. The MEDPOR® substrate has an average pore size greater than about 100 µm and a porosity of about 50% on one side of its surface and another side of its surface is solid and non-porous. The MEDPOR® substrate is affixed to the soft PVA component by applying silicone based primer and an adhesive to the non-porous surface of the MEDPOR® substrate and cured. The composite implant is then cured at room temperature for at least a day.

EXAMPLE 7

Soft Silicone Implant with MEDPOR® Anchors

A composite implant comprising a soft silicone (polysiloxane) component and porous HDPE anchors is produced according to the following procedure. MED-4244 is obtained from NuSil Technology of Carpinteria, Calif. Part A and Part B of MED-4244 are mixed in container in a 10:1 ratio of Part A to Part B in accordance with the product instructions. A vacuum is applied to the mixture to remove any air bubbles. 10 grams of the silicone mixture are poured into the 3-mm deep cavity of an aluminum sheet mold. MEDPOR® anchors are obtained from Porex Surgical, Inc. of Newnan, Ga. These MEDPOR® anchors display a cylindrical shape with a radius of 2 mm and a length of 5 mm. The MEDPOR® anchors have average pore size greater than about 100 µm and a porosity of about 50%. The MEDPOR® anchors are affixed to the cores of the mold, and the cores are inserted into the mold cavity containing the silicone mixture. When the cores are inserted into the cavity of the mold, the silicone mixture and MEDPOR® anchors are placed into contact.

The mold is subsequently placed in a hot press at 177° C. for five minutes to cure the silicon mixture. The mold is removed from the oven and allowed to cool to room temperature. The mold is disassembled, and the composite implant comprising a soft silicone component and porous HDPE anchors is removed. The composite implant is later cured at 150° C. for about 1 hour in an oven for a completed cure.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. A composite implant comprising:
   a soft polymeric component;
   a porous polymeric substrate; and
   a non-porous barrier located at an interface between the soft polymeric component and the porous polymeric substrate,
   wherein the soft polymeric component and the porous polymeric substrate are preformed with corresponding male and female coupling sites, each of the male coupling sites projecting outwardly from an outer surface of one of the soft polymeric component and the porous polymeric substrate and each of the female coupling sites being a recess located within the other of the soft polymeric component and the porous polymeric substrate,
   wherein the soft polymeric component is mechanically coupled to the porous polymeric substrate through engagement of a plurality of the male and female coupling sites at the interface between the soft polymeric component and the porous polymeric substrate, and wherein the male coupling sites pass through the non-porous barrier.

2. The implant of claim 1, wherein the porous polymeric substrate comprises at least one porous polymeric layer.

3. The implant of claim 1, wherein the porous polymeric substrate comprises a polyolefin, polyester, polyamide, polyketone, polacrylate, polymethylmethacrylate or polytetrafluoroethylene, or a combination thereof.

4. The implant of claim 3, wherein the polyolefin comprises polyethylene, polypropylene, and/or a copolymer thereof.

5. The implant of claim 4, wherein the polyethylene comprises high density polyethylene or ultrahigh molecular weight polyethylene.

6. The implant of claim 1, wherein the porous polymeric substrate is sintered porous plastic and comprises a plurality of polymeric particles.

7. The implant of claim 1, wherein the porous polymeric substrate has an average pore size ranging from about 1 um to about 1 mm and a porosity ranging from about 10% to about 90%.

8. The implant of claim 1, wherein the porous polymeric substrate has a Shore D hardness greater than about 30.

9. The implant of claim 1, wherein the porous polymeric substrate has a thickness ranging from about 0.2 mm to about 25 mm.

10. The implant of claim 1, wherein the soft polymeric component comprises at least one polymeric layer.

11. The implant of claim 1, wherein the soft polymeric component comprises polysiloxane, poly(vinyl alcohol), poly(vinyl alcohol) hydrogel, polytetrafluoroethylene, expanded-polytetrafluoroethylene or polyurethane, or a combination thereof.

12. The implant of claim 1, wherein the soft polymeric component comprises poly(vinyl alcohol) or poly(vinyl alcohol) hydrogel having a molecular weight of from about 100,000 to about 500,000.

13. The implant of claim 1, wherein the soft polymeric component comprises polysiloxane having a degree of polymerization of at least 1,000.

14. The implant of claim 1, wherein the soft polymeric component has a Shore A hardness greater than about 20.

15. The implant of claim 1, wherein the soft polymeric component has a tensile strength from about 3 MPa to about 10 MPa.

16. The implant of claim 1, wherein the soft polymeric component is non-porous.

17. The implant of claim 1, wherein the soft polymeric component is porous and has an average pore size ranging from about 1 um to about 1 mm and a porosity ranging from about 10% to about 90%.

18. The implant of claim 1, wherein the soft polymeric component has a thickness ranging from about 0.2 mm to about 100 mm.

19. The implant of claim 1, wherein the soft polymeric component is further coupled to the porous polymeric substrate through chemical means.

20. The implant of claim 1, wherein the mechanical coupling is further through the pores of the porous polymeric substrate.

21. The implant of claim 19, wherein the chemical means comprise an adhesive.

22. The implant of claim 21, wherein the adhesive comprises a silicone.

23. The implant of claim 1, wherein the implant is a craniofacial implant.

24. The implant of claim 23, wherein the craniofacial implant is a chin implant, malar implant, eye implant, ear implant or nose implant.

25. The implant of claim 1, wherein the soft polymeric component is non-porous and the porous polymeric substrate is sintered with an average pore size between 50 microns to 500 microns.

26. The implant of claim 1, wherein each of the respective male and female coupling sites has substantially the same shape as each other respective male or female coupling site and substantially the same thickness as the respective component or substrate.

27. The implant of claim 1, wherein the plurality of male coupling sites are metallic fasteners.

* * * * *